(12) United States Patent
Aoyama et al.

(10) Patent No.: US 7,816,110 B2
(45) Date of Patent: Oct. 19, 2010

(54) PROCESS FOR PRODUCING PELLETS CONTAINING ENTRAPPED MICROORGANISMS

(75) Inventors: Koutarou Aoyama, Tokyo (JP); Naoki Abe, Tokyo (JP); Tatsuo Sumino, Tokyo (JP); Hiroyoshi Emori, Tokyo (JP)

(73) Assignee: Hitachi Plant Technologies, Ltd., Tokyo (JP)

( * ) Notice: Subject to any disclaimer, the term of this patent is extended or adjusted under 35 U.S.C. 154(b) by 772 days.

(21) Appl. No.: 11/637,114

(22) Filed: Dec. 12, 2006

(65) Prior Publication Data

US 2007/0138089 A1 Jun. 21, 2007

(30) Foreign Application Priority Data

Dec. 15, 2005 (JP) .............................. 2005-362319

(51) Int. Cl.
- *C12N 11/04* (2006.01)
- *C12N 11/02* (2006.01)
- *C12N 1/04* (2006.01)

(52) U.S. Cl. ..................... 435/182; 435/177; 435/260

(58) Field of Classification Search .................. None
See application file for complete search history.

(56) References Cited

U.S. PATENT DOCUMENTS

| 4,634,672 | A | | 1/1987 | Baumgarten et al. |
| 4,681,851 | A | | 7/1987 | Baumgarten et al. |
| 4,791,061 | A | * | 12/1988 | Sumino et al. .............. 435/178 |

FOREIGN PATENT DOCUMENTS

| EP | 0 121 851 | A2 | 10/1984 |
| GB | 2 116 997 | A | 10/1983 |
| GB | 2 386 124 | A | 9/2003 |
| JP | A-3-254892 | | 11/1991 |
| JP | A 08-323381 | | 12/1996 |
| JP | A 10-290992 | | 11/1998 |
| JP | A 2002-136984 | | 5/2002 |
| JP | A 2002-159985 | | 6/2002 |
| JP | A 2003-200183 | | 7/2003 |
| JP | A 2003-235553 | | 8/2003 |
| JP | A 2004-41981 | | 2/2004 |
| JP | A-2004-275796 | | 10/2004 |

OTHER PUBLICATIONS

H. Büyükgüngör, "Stability of *Lactobacillus bulgaricus* Immobilized in κ-Carrageenan Gels", Journal of Chemical Technology and Biotechnology, vol. 53, No. 2, Jan. 1992, pp. 173-175.

K. Park et al., "Immobilization as a Technical Possibility for Long-Term Storage of Bacterial Biosensors", Radiation and Environmental Biophysics, vol. 44, No. 1, May 2005, pp. 69-71.

J. Bjerketorp et al., "Advances in Preservation Methods: Keeping Biosensor Microorganisms Alive and Active", Current Opinion in Biotechnology, vol. 17, No. 1, 2006, pp. 43-49.

May 11, 2010 Office Action issued in corresponding Chinese Patent Application No. 200610168461.5 (w/translation).

* cited by examiner

*Primary Examiner*—David M Naff
(74) *Attorney, Agent, or Firm*—Oliff & Berridge, PLC

(57) ABSTRACT

A process for storing entrapping immobilization pellets in which microorganisms are entrapped and immobilized in an immobilizing material until the entrapping immobilization pellets are used in a treatment tank, the process comprising: storing a large pellet block in water at 15° C. or less or in air at a relative humidity of 90% or more and a temperature of 15° C. or less until the pellet block is cut into the entrapping immobilization pellets and used.

4 Claims, 6 Drawing Sheets

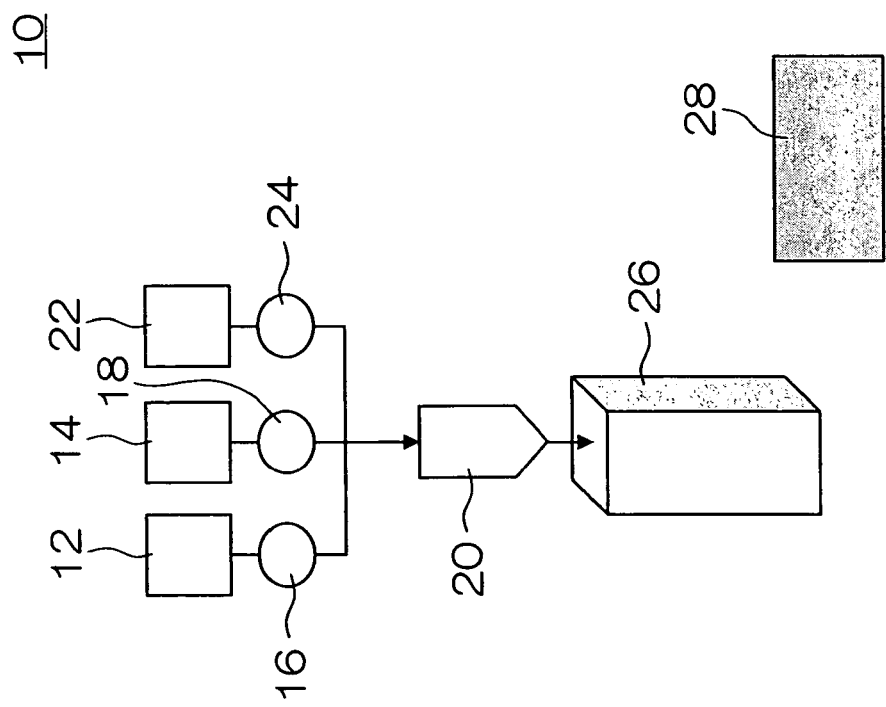

PROCESS FOR PRODUCING PELLETS CONTAINING ENTRAPPED MICROORGANISMS

BACKGROUND OF THE INVENTION

1. Field of the Invention

The present invention relates to storage and production processes for entrapping immobilization pellets. More particularly, the present invention relates to storage and production processes for entrapping immobilization pellets suitable for wastewater treatment in order to remove nitrogen.

2. Description of the Related Art

Conventionally, as a process for treating wastewater such as sewage, industrial wastewater or agricultural wastewater, a biological process has been widely used, because the process involves a low cost as compared with a physicochemical process. Typical examples include an activated sludge process used for sewage. However, since slowly growing microorganisms such as nitrifying bacteria in activated sludge which are highly involved in removing organic substances or nitrogen in wastewater flow out of a reaction tank without sufficient growth, the reaction speed is significantly decreased particularly when the water temperature is low, resulting in deterioration of water quality. In this situation, a wastewater treatment process using attachment immobilization pellets in which microorganisms are attached to and immobilized on resin systems and plastic pellets (see Japanese Patent Application Laid-Open Nos. 2002-159985 and 2004-41981, for example) and a tap water treatment process using biologically activated carbon (see Japanese Patent Application Laid-Open Nos. 2003-200183 and 10-290992, for example) have been practically used for retaining microorganisms such as nitrifying bacteria in a treatment tank at a high concentration and stably. There has also been performed a wastewater treatment process comprising producing entrapping immobilization pellets in which microorganisms such as nitrifying bacteria are entrapped and immobilized in an immobilizing material, and packing a wastewater treatment tank with the entrapping immobilization pellets to increase the concentration of nitrifying bacteria.

However, in the wastewater treatment process using attachment immobilization pellets, the attached microorganisms are detached from the pellets, or microorganisms differing from target microorganisms such as nitrifying bacteria are attached to the pellets, making it difficult to sufficiently retain the target microorganisms. In contrast, in the wastewater treatment process using entrapping immobilization pellets, target microorganisms can be acclimatized in the pellets and thus can be retained in the pellets at a high concentration. Accordingly, wastewater can be treated fast.

Such entrapping immobilization pellets are produced by tube forming, dropping granulation, sheet forming or the like. Tube forming is a process comprising injecting a mixture of microorganisms with a polymer material into a vinyl tube having a diameter of several millimeters to polymerize and extrude the mixture, and cutting the mixture into cylindrical pellets with a certain length. This process can provide pellets with high form accuracy, but is not suitable for mass production. Dropping granulation is a process comprising dropping a mixture of microorganisms with a polymer material into a separate liquid to produce spherical pellets. This process allows easy mass production, but has a drawback in that the produced pellets have various particle sizes. Sheet forming is a process comprising forming a mixture of microorganisms with a polymer material into a sheet and finely cutting the sheet into rectangular pellets (see Japanese Patent Application Laid-Open No. 2003-235553). Entrapping immobilization pellets are often produced by sheet forming for wastewater treatment equipment requiring a large amount of pellets, because this process provides high form accuracy and is suitable for mass production.

However, since oxygen in air generally reacts with radicals, contact of an immobilizing material with air causes suppression of immobilization of microorganisms on the immobilizing material. Sheet forming provides a large contact area between an immobilizing material and air, and thus has drawbacks in that pellet strength is decreased due to unstable polymerization, and COD flows out due to the remaining unpolymerized material when entrapping immobilization pellets are introduced, for example.

As a device to solve these drawbacks, the present inventors have filed a patent application for block forming. The block forming is a process comprising injecting and immobilizing a liquid mixture of microorganisms with an immobilizing material (polymer material) in an almost cubic or rectangular solid forming frame to reduce the contact area between the immobilizing material and air. This can suppress a decrease or variation in pellet strength or the presence of the remaining unpolymerized material due to contact of the immobilizing material with air.

Typically, such entrapping immobilization pellets are granulated by forming a pellet into a sheet or block and cutting the pellet into about 3 mm squares in a production plant (granulation plant), and then stored and transported to a treatment tank into which the entrapping immobilization pellets are to be introduced.

However, in the conventional process for storing and transporting entrapping immobilization pellets, entrapping immobilization pellets brought into contact with each other are easily caused to adhere to each other and aggregated into balls, resulting in a decrease in wastewater treatment efficiency. For this reason, when transported, entrapping immobilization pellets must be dipped in water whose weight is almost equal to that of the entrapping immobilization pellets. This involves a heavy work load, disadvantageously, because about twice the weight of necessary entrapping immobilization pellets must be transported.

When storing and transporting a pellet block still to be cut into pellets in normal air for a long time as is in order to reduce the above-described work load during storage and transportation, only the outside of the pellet block is dried, and the aqueous content differs between the inside and the outside of the pellet block, making the pellet block deformed, disadvantageously. Moreover, microorganisms have increased activity and thus methane, hydrogen sulfide or the like is generated in the pellet block to produce cracks in the pellet block, resulting in a variation in shape or quality of the entrapping immobilization pellets obtained by cutting the pellet block, disadvantageously.

The present invention has been achieved in view of such circumstances. An object of the present invention is to provide storage and production processes for entrapping immobilization pellets which can stably store and transport a pellet block and can provide entrapping immobilization pellets having high quality stability.

SUMMARY OF THE INVENTION

To attain the aforementioned object, according to a first aspect of the present invention, there is provided a process for storing entrapping immobilization pellets in which microorganisms are entrapped and immobilized in an immobilizing material until the entrapping immobilization pellets are used in a treatment tank, the process comprising storing a large pellet block in water at 15° C. or less or in air at a relative humidity of 90% or more and a temperature of 15° C. or less until the pellet block is cut into the entrapping immobilization pellets and used.

The present inventors have noted the fact that work load for storing and transporting entrapping immobilization pellets can be reduced by storing and transporting a pellet block as is until the pellet block is cut into entrapping immobilization pellets and used, rather than conventionally storing and transporting entrapping immobilization pellets obtained by previously cutting a pellet block.

Further, as a result of extensive studies on the process and conditions for storing a pellet block in a more stable manner, the present inventors have found a process and conditions for storing a pellet block which can stably store and transport a pellet block and can provide entrapping immobilization pellets having high quality stability.

According to the present invention, a large pellet block is stored in water at 15° C. or less or in air at a relative humidity of 90% or more and a temperature of 15° C. or less until the pellet block is cut into entrapping immobilization pellets and used.

This can reduce the occurrence of drawbacks in that the surface of the pellet block is dried and the aqueous content differs between the inside and the surface of the pellet block, making the pellet block deformed, and gas is generated from within the pellet block to produce cracks in the pellet block, for example, when the pellet block is stored. A variation in shape or quality of the resulting entrapping immobilization pellets can thus be suppressed when the pellet block is cut into the pellets. Further, when the pellet block is stored in water, the amount of water used can be considerably reduced as compared with a conventional case.

The pellet block refers to a block-shaped pellet in which microorganisms are entrapped and immobilized in an immobilizing material, and is still to be cut into entrapping immobilization pellets. The pellet block mainly has an almost cubic or rectangular solid shape, but may have another shape such as a cylindrical shape. The relative humidity refers to a relative humidity at room temperature (about 20° C.).

According to a second aspect of the present invention, there is provided the process for storing entrapping immobilization pellets according to the first aspect, wherein the pellet block is almost cubic and has a length:width:depth ratio of 1:1:1 to 1:1:20.

As a result of various studies on the storage conditions for a pellet block, the present inventors have found appropriate ranges of size and shape of a pellet block. Entrapping immobilization pellets having high quality stability can thus be obtained.

Specifically, according to the second aspect, wherein the pellet block is almost cubic and has a length:width:depth ratio of 1:1:1 to 1:1:20, pressure may be relatively uniformly applied to the pellet block when the pellet block is cut into pellets, and workability can be improved when the pellet block is transported, for example. The pellet block preferably has a length:width:depth ratio of 1:1:3 to 1:1:7.

According to a third aspect of the present invention, there is provided the process for storing entrapping immobilization pellets according to the first or second aspect, wherein the pellet block has a bottom length:bottom width ratio of 50 mm:50 mm to 150 mm:150 mm and a volume of 0.12 L to 22.5 L.

The third aspect, wherein the pellet block has a bottom length:bottom width ratio of 50 mm:50 mm to 150 mm:150 mm and a volume of 0.12 L to 22.5 L, can suppress production of cracks in the pellet block caused by gas generation due to an anaerobic condition in the pellet block, and further can prevent reduction in productivity.

Thus, the pellet block can be stably stored and transported, and entrapping immobilization pellets having high quality stability can be obtained. The pellet block preferably has a volume of 2.4 L to 7.3 L.

To attain the aforementioned object, according to a fourth aspect of the present invention, there is provided a process for producing entrapping immobilization pellets in which microorganisms are entrapped and immobilized in an immobilizing material, the process comprising polymerizing a liquid mixture of the microorganisms with the immobilizing material into a gel to form a pellet block larger than the entrapping immobilizing pellets for use; storing the pellet block in water at 15° C. or less or in air at a relative humidity of 90% or more and a temperature of 15° C. or less until the entrapping immobilization pellets are used; and cutting the stored pellet block into the entrapping immobilization pellets for use.

According to the present invention, a liquid mixture of the microorganisms with the immobilizing material is polymerized into a gel to form a pellet block larger than the entrapping immobilization pellets for use; the pellet block is stored in water at 15° C. or less or in air at a relative humidity of 90% or more and a temperature of 15° C. or less until the entrapping immobilization pellets are used; and the stored pellet block is cut into the entrapping immobilization pellets for use. Thus, the pellet block can be stably stored and transported, and entrapping immobilization pellets having high quality stability can be obtained.

According to a fifth aspect of the present invention, there is provided the process for producing entrapping immobilization pellets according to the fourth aspect, wherein the pellet block is prepared by polymerizing a liquid mixture of the microorganisms with the immobilizing material into a gel in an almost cubic forming frame, and the length:width:depth ratio in the forming frame is 1:1:1 to 1:1:20.

The pellet block of the second aspect can be prepared according to the fifth aspect, wherein the pellet block is prepared by polymerizing a liquid mixture of the microorganisms with the immobilizing material into a gel in an almost cubic forming frame, and the length:width:depth ratio in the forming frame is 1:1:1 to 1:1:20. Thus, the pellet block can be stably stored and transported, and entrapping immobilization pellets having high quality stability can be obtained. The length:width:depth ratio in the forming frame is preferably 1:1:3 to 1:1:7.

According to a sixth aspect of the present invention, there is provided the process for producing entrapping immobilization pellets according to the fourth or fifth aspect, wherein the bottom length:bottom width ratio in the forming frame is 50 mm:50 mm to 150 mm:150 mm, and the pellet block has a volume of 0.12 L to 22.5 L.

The pellet block of the third aspect can be produced according to the sixth aspect. Thus, the pellet block can be stably stored and transported, and entrapping immobilization pellets having high quality stability can be obtained.

According to a seventh aspect of the present invention, there is provided the process for producing entrapping immobilization pellets according to any one of the fourth to sixth aspects, the process comprising cutting the pellet block into lattices; cutting the lattices into 1 mm to 10 mm-square almost cubic entrapping immobilization pellets; and introducing the entrapping immobilization pellets into a treatment tank.

According to the seventh aspect of the present invention, the pellet block is cut into lattices; the lattices are cut into 1 mm to 10 mm-square almost cubic entrapping immobilization pellets; and the entrapping immobilization pellets are introduced into a treatment tank. Thus, the pellet block can be stably stored and transported, and entrapping immobilization pellets having high quality stability can be obtained.

According to the present invention, a pellet block can be stably stored and transported, and entrapping immobilization pellets having high quality stability can be obtained.

BRIEF DESCRIPTION OF THE DRAWINGS

FIG. 1 is a view describing a pellet block production apparatus in the present embodiment;

DETAILED DESCRIPTION OF THE PREFERRED EMBODIMENTS

Figure 2A:
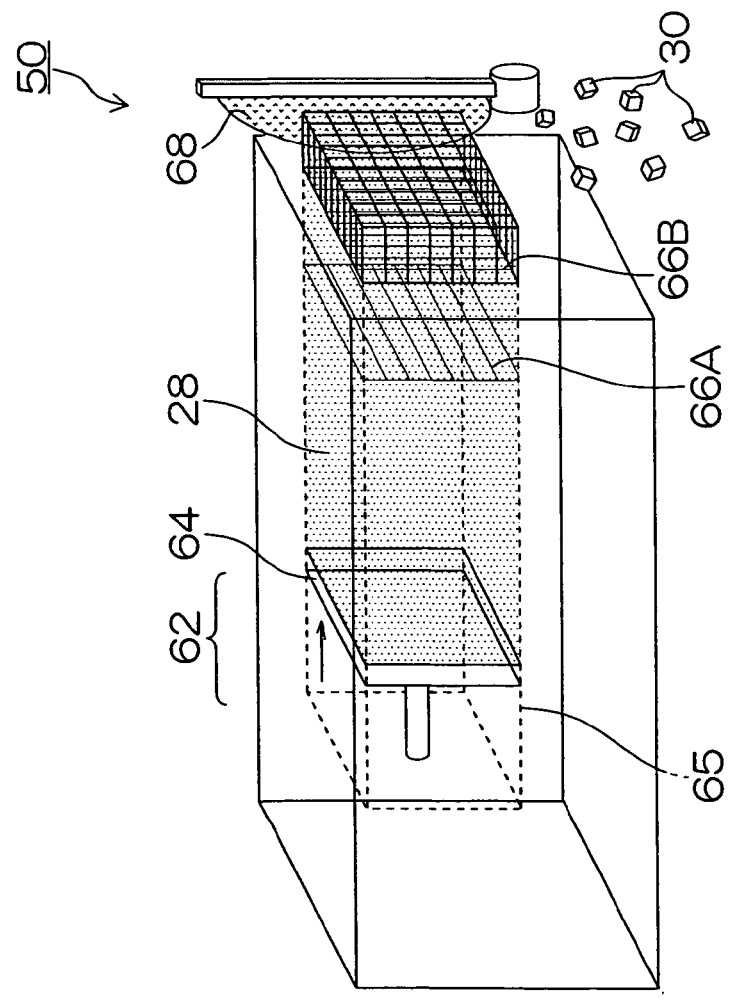
FIGS. 2A and 2B are views describing a pellet block cutting apparatus in the present embodiment.

A preferred embodiment of the storage and production processes for entrapping immobilization pellets according to the present invention will be described in detail below with reference to the accompanying drawings.

Configurations of various apparatus for producing entrapping immobilization pellets in the present embodiment (FIGS. 1 and 2) will be described first.

FIG. 1 is a view describing a configuration of a pellet block production apparatus 10.

As shown in FIG. 1, the pellet block production apparatus 10 comprises, as main components, a raw material tank 12 for storing a raw material, chemical tanks 14, 22 for storing chemicals, a stirring and extrusion unit 20 for mixing the raw material with the chemicals, and a forming frame 26 for polymerizing the liquid mixture to produce a pellet block 28.

In the raw material tank 12, microorganisms (such as activated sludge) as a raw material are stored. In the chemical tank 14, a chemical such as an immobilizing material is stored. In the chemical tank 22, a chemical such as a polymerization initiator is stored.

Pumps 16, 18, 24 are driving devices of introducing the raw material in the raw material tank 12, the chemical in the chemical tank 14, and the chemical in the chemical tank 22 into the stirring and extrusion unit 20, respectively, and are provided between the stirring and extrusion unit 20 and the raw material tank 12, the chemical tank 14, and the chemical tank 22, respectively. Thus, a liquid mixture as a raw material for producing entrapping immobilization pellets can be prepared in the stirring and extrusion unit 20 and extruded into the forming frame 26.

The forming frame 26 is a container in which the liquid mixture extruded from the stirring and extrusion unit 20 is polymerized. The forming frame 26 is preferably provided with a heating device for accelerating polymerization of the liquid mixture.

Preferably, the bottom length:bottom width ratio in the forming frame 26 can be controlled in the range of 50 mm:50 mm to 150 mm:150 mm.

Microorganisms that can be immobilized are bacteria contained in activated sludge, which are complex microorganisms comprising nitrifying bacteria, denitrifying bacteria, and anaerobic ammonium oxidizing bacteria. In order to increase the initial immobilizing concentration of the target microorganisms, the activated sludge concentration is preferably 10,000 mg-ss/L to 40,000 mg-ss/L. Pure microorganisms such as microcystis decomposing bacteria, PCB decomposing bacteria, dioxin decomposing bacteria, and environmental hormone decomposing bacteria can also be used.

The microorganisms refer not only to microorganisms concentrated and separated by culturing, but also to substances containing various microorganisms such as activated sludge in sewage treatment plants, sludge in lakes, rivers, or sea, and soil. Examples of the immobilizing material used include, but are not limited to, the following materials:

monomethacrylates such as polyethylene glycol monomethacrylate, polyprene glycol monomethacrylate, polypropylene glycol monomethacrylate, methoxydiethylene glycol methacrylate, methoxypolyethylene glycol methacrylate, methacryloyloxyethyl hydrogen phthalate, methacryloyloxyethyl hydrogen succinate, 3-chloro-2-hydroxypropyl methacrylate, stearyl methacrylate, 2-hydroxy methacrylate, and ethyl methacrylate;

monoacrylates such as 2-hydroxyethyl acrylate, 2-hydroxypropyl acrylate, isobutyl acrylate, t-butyl acrylate, isooctyl acrylate, lauryl acrylate, stearyl acrylate, isobornyl acrylate, cyclohexyl acrylate, methoxytriethylene glycol acrylate, 2-ethoxyethyl acrylate, tetrahydrofurfuryl acrylate, phenoxyethyl acrylate, nonylphenoxypolyethylene glycol acrylate, nonylphenoxypolypropylene glycol acrylate, silicon-modified acrylate, polypropylene glycol monoacrylate, phenoxyethyl acrylate, phenoxydiethylene glycol acrylate, phenoxypolyethylene glycol acrylate, methoxypolyethylene glycol acrylate, acryloyloxyethyl hydrogen succinate, and lauryl acrylate;

dimethacrylates such as 1,3-butylene glycol dimethacrylate, 1,4-butanediol dimethacrylate, ethylene glycol dimethacrylate, diethylene glycol dimethacrylate, triethylene glycol dimethacrylate, polyethylene glycol dimethacrylate, butylene glycol dimethacrylate, hexanediol dimethacrylate, neopentyl glycol dimethacrylate, polyprene glycol dimethacrylate, 2-hydroxy-1,3-dimethacryloxypropane, 2,2-bis-4-methacryloxyethoxyphenylpropane, 3,2-bis-4-methacryloxydiethoxyphenylpropane, and 2,2-bis-4-methacryloxypolyethoxyphenylpropane;

diacrylates such as ethoxylated neopentyl glycol diacrylate, polyethylene glycol diacrylate, 1,6-hexanediol diacrylate, neopentyl glycol diacrylate, tripropylene glycol diacrylate, polypropylene glycol diacrylate, 2,2-bis-4-acryloxyethoxyphenylpropane, 2-hydroxy-1-acryloxy-3-methacryloxypropane;

trimethacrylates such as trimethylolpropane trimethacrylate;

triacrylates such as trimethylolpropane triacrylate, pentaerythritol triacrylate, trimethylolpropane EO-added triacrylate, glycerol PO-added triacrylate, and ethoxylated trimethylolpropane triacrylate;

tetraacrylates such as pentaerythritol tetraacrylate, ethoxylated pentaerythritol tetraacrylate, propoxylated pentaerythritol tetraacrylate, and ditrimethylolpropane tetraacrylate;

urethane acrylates such as urethane acrylate, urethane dimethyl acrylate, and urethane trimethyl acrylate; and other compounds such as acrylamide, acrylic acid, and dimethylacrylamide.

The immobilizing materials may be used singly or in a combination of two or more. A prepolymer having a molecular weight of 4,000 or more is preferably used in the present embodiment.

The concentration of the immobilizing material is preferably 3 mass % to 10 mass % based on the mass of entrapping immobilization pellets. The immobilizing material is preferably used as an immobilizing material solution prepared with water.

The polymerization in the present embodiment is most appropriately radical polymerization using potassium persulfate, but may be polymerization using ultraviolet rays or electron beams or redox polymerization. In polymerization using potassium persulfate, it is preferable to add 0.001 mass % to 0.25 mass % of potassium persulfate and 0.001 mass % to 0.5 mass % of a polymerization accelerator. As the polymerization accelerator, β-dimethylaminopropionitrile, N,N,N',N'-tetramethylethylenediamine, sodium sulfite, or the like is preferably used.

Next, there will be described a pellet block cutting apparatus 50 in which the pellet block 28 is cut into entrapping immobilization pellets 30.

Figure 2B:
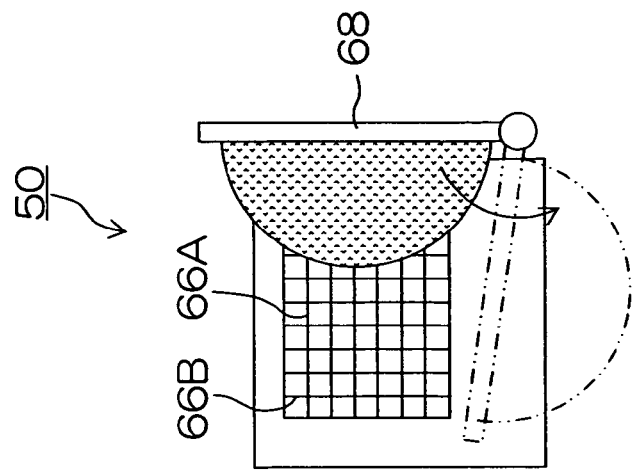

FIGS. 2A and 2B are views describing a pellet block cutting apparatus 50.

As shown in FIGS. 2A and 2B, the pellet block cutting apparatus 50 comprises a transport device 62 and an extrusion board 64 which transport the pellet block 28 while fixing, lattice-shaped cutting blades 66A, 66B, and a rotary cutting blade 68 as main components.

The transport device 62 and the extrusion board 64 are configured to extrude the pellet block 28 into the lattice-shaped cutting blades 66A, 66B at a predetermined speed. Specifically, the extrusion board 64 is movable by the transport device 62 such as a ball screw mechanism or a cylinder mechanism which can control the transport speed, for example.

The multiple lattice-shaped cutting blades 66A and the multiple lattice-shaped cutting blades 66B are provided at predetermined intervals in the shape of lattices, respectively. The lattice-shaped cutting blades 66A and the lattice-shaped cutting blades 66B in FIGS. 2A and 2B are located two-dimensionally perpendicular to each other in multiple stages.

As the lattice-shaped cutting blades 66A, 66B, wire saws or cutter blades arranged in the shape of lattices can be used. In the present embodiment, in order to produce the 3 mm-square cubic entrapping immobilization pellets 30, lattice-shaped cutting blades provided at intervals of about 3 mm each are preferably used.

The rotary cutting blade 68 cuts the pellet block 28, cut into about 3 mm-narrow lattices, perpendicular to the transport direction at a predetermined rotation speed.

A thin cutting blade having a thickness of 1 mm, for example, is used for the lattice-shaped cutting blades 66A, 66B or the rotary cutting blade 68. In the present embodiment, the entrapping immobilization pellets each preferably have a size of 1 mm to 10 mm squares.

The present embodiment employs lattice-shaped cutting blades arranged in multiple stages and a rotary cutting blade. However, the lattice-shaped cutting blades 66 may be mesh-shaped cutting blades perpendicular to each other and arranged in the shape of a mesh, and the rotary cutting blade 68 may be replaced with a guillotine cutting blade.

Next, the process for producing entrapping immobilization pellets 30 will be described with reference to FIGS. 1 and 2. First, as shown in FIG. 1, a raw material in a raw material tank 12 (such as activated sludge) and a chemical in a chemical tank 14 (such as an immobilizing material) are mixed and fed into a stirring and extrusion unit 20 by driving pumps 16, 18. Then, the liquid mixture fed into the stirring and extrusion unit 20 is mixed with a chemical fed thereinto from another chemical tank 22 by a pump 24 (such as a polymerization initiator), followed by stirring. The liquid mixture is subsequently extruded into a forming frame 26.

Thereafter, the liquid mixture is polymerized into a gel in the forming frame 26 heated to 20 to 30° C. In this case, the liquid mixture contains an immobilizing material, water, activated sludge, a polymerization initiator, a polymerization accelerator, and the like. Polymerization reaction proceeds for 10 to 60 minutes to produce a gelled pellet block 28. The gelled pellet block 28 was then taken from the forming frame 26.

The pellet block 28 is then cut into lattices by lattice-shaped 66A, 66B while being transported by a transport device 62 at a predetermined transport speed in a fixing stage 65 of a pellet block cutting apparatus 50 in FIGS. 2A and 2B. Next, The pellet block 28, cut into lattices, is further cut into 3 mm-square almost cubic entrapping immobilization pellets 30 with a rotary cutting blade 68.

The entrapping immobilization pellets 30 are introduced into a treatment tank and used for various treatments.

In the above process for producing entrapping immobilization pellets, it is possible to cut the pellet block 28 while continuously forming the pellet block 28 to produce the entrapping immobilization pellets 30, and then dip the pellets in a large amount of water to store and transport the pellets. However, it is preferable in terms of working efficiency and performance of the entrapping immobilization pellets that the pellet block 28 is stored as is and cut into only a necessary amount of 3 mm-square almost cubic pellets using the cutting apparatus 50 in FIGS. 2A and 2B, for example, when or where the pellets are needed. On the other hand, it has been confirmed that, when the pellet block 28 is allowed to stand in air for long term as is, gas is generated from within the pellet block 28, and the surface of the pellet block 28 is dried to deform the pellet block 28, resulting in a variation in the shape of the 3 mm-square almost cubic entrapping immobilization pellets, disadvantageously.

The present invention is characterized in that the pellet block 28 before pelletization is stably stored and transported in order to reduce work load during transportation and improve quality stability of the entrapping immobilization pellets.

The process for storing a pellet block 28 according to the present invention will be described in detail below.

Figure 3:
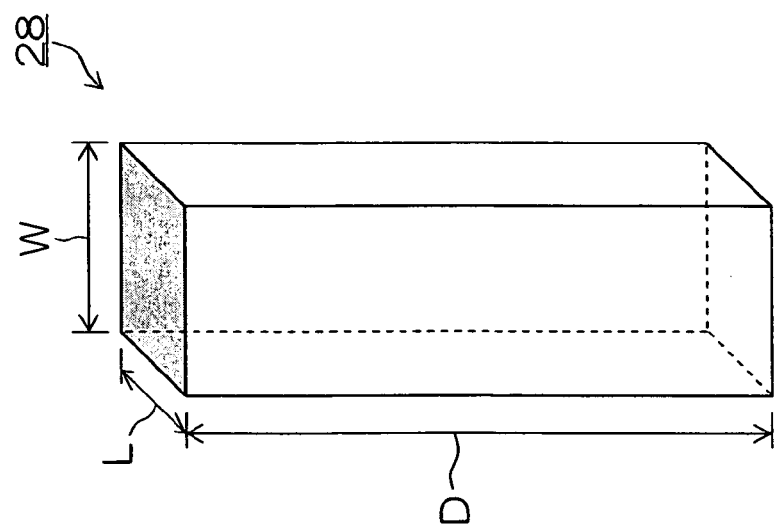
FIG. 3 is an oblique view describing a pellet block in the present embodiment.

FIG. 3 is an oblique view describing the pellet block 28. In FIG. 3, the symbol L denotes a bottom length of the pellet block 28, the symbol W denotes a bottom width of the pellet block 28, and the symbol D denotes a depth of the pellet block 28.

As shown in FIG. 3, the pellet block 28 is mainly almost cubic or rectangular solid, and has a length (L):width (W): depth (D) ratio of preferably 1:1:1 to 1:1:20, and more preferably 1:1:3 to 1:1:7.

Specifically, when the pellet block 28 has a length:width ratio of 1:1, pressure can be uniformly applied to the pellet block 28 when the pellet block 28 is cut, and the pellet block 28 can be cut into 3 mm-square almost cubic entrapping immobilization pellets having shape stability. If the depth of the pellet block 28 is too larger than the length or width of the pellet block, the pellet block 28 is easily broken when transported to or introduced into a cutting apparatus 50. On the other hand, if the depth is too smaller than the length or width, production capacity is decreased. If the pellet block 28 has a shape within the above range, the pellet block 28 is difficult to have such drawbacks.

The pellet block 28 preferably has a bottom length:bottom width ratio of 50 mm:50 mm to 150 mm:150 mm and a volume of 0.12 L to 22.5 L. The pellet block more preferably has a volume of 2.4 L to 7.3 L.

The pellet block 28 having a volume and a shape within the above range can be produced without decreased productivity and easily handled. Further, it is possible to suppress production of cracks in the pellet block 28 caused by gas generation due to an anaerobic condition in the pellet block.

The pellet block 28 is preferably stored in water at 15° C. or less or in air at a relative humidity of 90% or more and a temperature of 15° C. or less.

This is because, when the pellet block 28 is allowed to stand in normal air, the surface of the pellet block 28 is dried, and thus the aqueous content differs between the inside and the outside of the pellet block 28, making the pellet block 28 deformed. This is also because gas generation should be suppressed in the pellet block 28, since cell activity is increased in the pellet block 28 at a storage temperature of more than 15° C.

The relative humidity refers to a relative humidity at room temperature (about 20° C.).

Examples of the process of storing the pellet block 28 at such relative humidity and storage temperature include, but are not limited to, a process of storing the pellet block in a known thermo-hygrostat, a process of storing the pellet block together with a sponge containing water, and a process of storing the pellet block in a water tank into which a small amount of water is introduced.

The above-described storage and production processes for entrapping immobilization pellets according to the present invention can stably store and transport a pellet block. Further, a necessary amount of entrapping immobilization pellets having high quality stability can be obtained when needed, because a pellet block 28 is cut into entrapping immobilization pellets when used.

An embodiment of the storage and production processes for entrapping immobilization pellets according to the present invention are as described above. However, the present invention is not limited to the above embodiment, and various embodiments are possible. The specification describes an example of the present embodiment in which a pellet block production apparatus 10 and a pellet block cutting apparatus 50 are separately configured. However, the embodiment is not limited to this example, and these apparatus may be integrally configured.

In the present embodiment, a pellet block 28 is formed by block forming in a forming frame 26. However, the forming process is not limited to block forming, and other forming processes such as sheet forming and tube forming may be applied to a part of the present invention.

EXAMPLE

An Example of the present invention will be described below. However, the present invention is not limited to the example. Entrapping immobilization pellets 30 had the following composition.

(Composition of Entrapping Immobilization Pellets 30)

Activated sludge: Sludge of nitrifying bacteria, 3.0 mass %

Concentration of cells of nitrifying bacteria: $5 \times 10^5$ cells/mL

Immobilizing material: Polyethylene glycol diacrylate, 10.0 mass %

Polymerization accelerator: N,N,N',N'-tetramethylethylenediamine, 0.5 mass %

Polymerization initiator: Potassium persulfate, 0.25 mass %

1) Storage Temperature and Humidity

First, a pellet block 28 having a volume of 4 L (length: 100 mm×width: 100 mm×depth: 400 mm) was stored at a temperature of 20° C. and a relative humidity of 60% to 90% for seven days. Deformation of the pellet block 28 at each humidity was visually observed. The results are shown in Table 1.

TABLE 1

| Relative humidity (%) | Deformation of pellet block 28 |
|---|---|
| 60 | Deformed |
| 70 | Deformed |
| 75 | Deformed |
| 80 | Deformed |
| 85 | Deformed |
| 90 | Not deformed |
| In water (2 L) | Not deformed |

As shown in Table 1, it was found that the surface of the pellet block 28 is not dried and the pellet block 28 is not deformed at a relative humidity of 90%. However, it was found that the surface of the pellet block 28 is dried and the pellet block 28 is deformed at a relative humidity of 60% to 85%.

The pellet block 28 was not deformed even when dipped and stored in water whose amount was about half or less the amount of water in a conventional case.

It was thus found that surface drying and deformation of the pellet block 28 can be suppressed when the pellet block 28 is stored at a relative humidity of 90% or more or in water. It was also found that, when the pellet block 28 is dipped and stored in water, the amount of water used can be reduced to about 50% or less as compared with a conventional case.

Next, a pellet block 28 having the same size (volume: 4 L) was dipped in about 2 L of water, stored at various temperatures for seven days, and cut into entrapping immobilization pellets 30 to determine shape variations of the resulting entrapping immobilization pellets 30.

A shape variation of the entrapping immobilization pellets 30 referred to a ratio of a mass of 1 mm or less-square entrapping immobilization pellets 30 and 5 mm or more-square entrapping immobilization pellets 30 to a mass of the pellet block 28 cut into about 3 mm-square entrapping immobilization pellets 30 (unit: %). The evaluation results are shown in FIG. 4.

Figure 4:
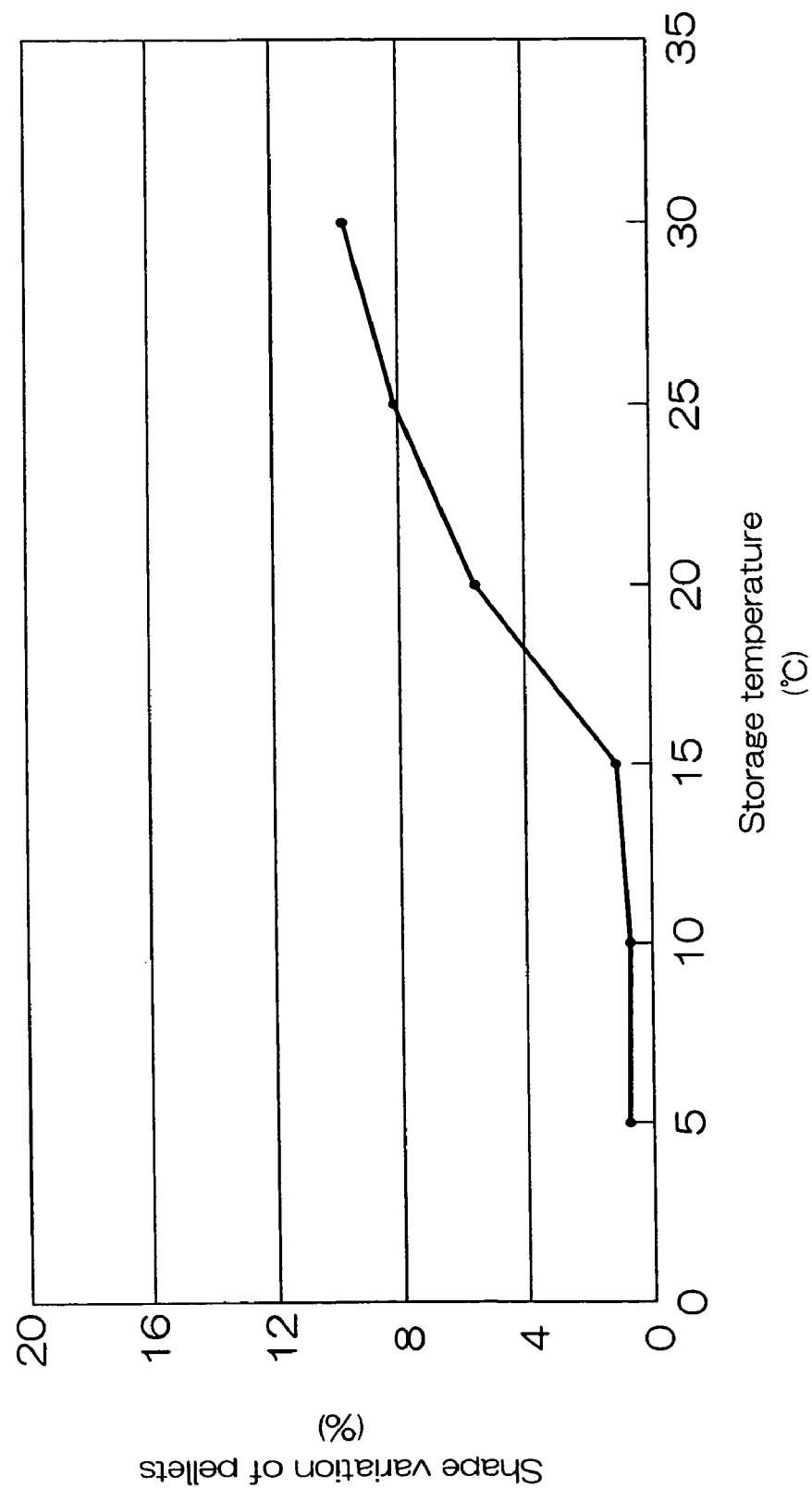
FIG. 4 is a graph for the example.

As shown in FIG. 4, when the pellet block 28 was stored at 15° C. or less, the shape variation of entrapping immobilization pellets 30 was as small as about 1% and acceptable. However, when the pellet block 28 was stored at 20° C. or more, cracks due to gas generation from within the pellet block 28 were confirmed. A large shape variation of the entrapping immobilization pellets 30 occurred when the pellet block 28 was cut into the entrapping immobilization pellets 30. This is presumably because microorganisms in the pellet block 28 have increased cell activity when the pellet block 28 is stored at 20° C. or more.

It was thus found that gas generation from within the pellet block 28 can be effectively suppressed when the pellet block 28 is stored at 15° C. or less.

2) Volume of Pellet Block 28

Various sizes (volumes) of pellet blocks 28 were stored in water at 15° C. for seven days to evaluate the presence or absence of gas generation from within the pellet block 28 and the shape variations of entrapping immobilization pellets. The results are shown in FIG. 5.

Figure 5:
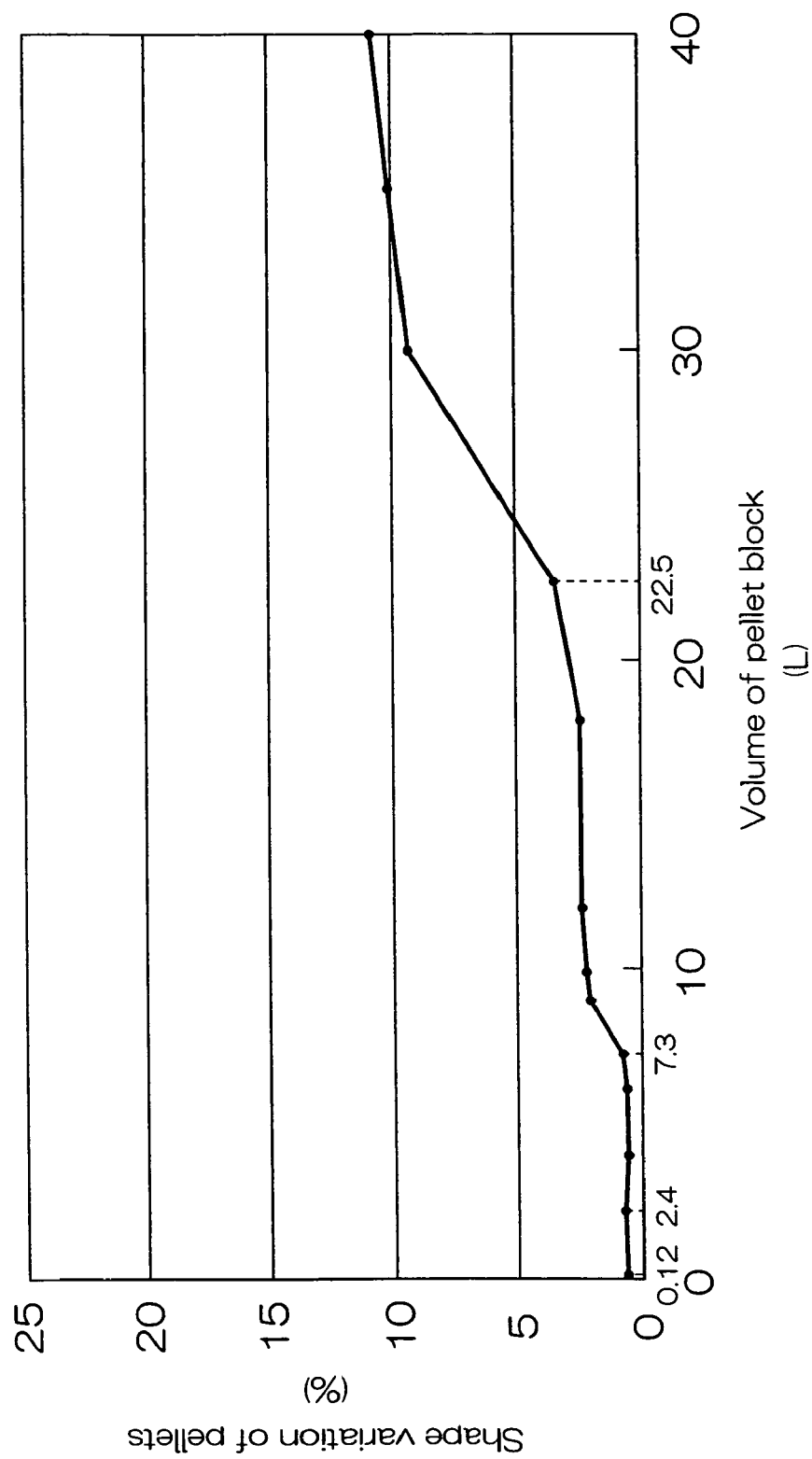
FIG. 5 is a graph for the example.

As shown in FIG. 5, the presence of bubbles presumably due to gas generation in the pellet block 28 was confirmed when the pellet block 28 had a volume of 30 L or more. As the amount of bubbles generated was increased, the shape variation of the entrapping immobilization pellets 30 was drastically increased.

On the other hand, when the pellet block 28 had a volume of 22.5 L or less, almost no cracks due to the presence of bubbles in the pellet block 28 were observed. This is presumably because the pellet block 28 had a small volume and thus the generated gas was easily escaped to outside.

Accordingly, the pellet block 28 has a volume of preferably 0.12 L to 22.5 L, and more preferably 2.4 L to 7.3 L.

3) Evaluation of Pellet Strength and Shape of Entrapping Immobilization Pellets

Five pellet blocks 28 (A to E) each having a volume of 4 L (length: 100 mm×width: 100 mm×depth: 400 mm) were prepared and stored in water at a temperature of 15° C. for seven days. Then, the pellet blocks 28 were cut into about 3 mm-square entrapping immobilization pellets 30 to determine shape variations and pellet strength of the entrapping immobilization pellets 30.

Pellet strength was determined using a rheometer as a compression force per unit area when the entrapping immobilization pellets 30 were compressed at a certain force to break the pellet gel. Shape variations of the entrapping immobilization pellets 30 were determined in the same manner as in the above 1). The results are shown in Table 2.

TABLE 2

| Pellet block 28 | Shape variation (%) | Pellet strength (kgf/cm$^2$) |
|---|---|---|
| A | 1.1 | 4.4 |
| B | 1.5 | 4.3 |
| C | 1.3 | 4.3 |
| D | 1.8 | 4.5 |
| E | 1.6 | 4.1 |

As shown in Table 2, each of the pellet blocks A to E had a small shape variation of 1.1% to 1.8%. Each of the pellet blocks A to E had a similar and high pellet strength of 4.1 kgf/cm$^2$ to 4.5 kgf/cm$^2$.

The pellet strength and shape of the entrapping immobilization pellets 30 were comparable or superior to those of entrapping immobilization pellets stored by a conventional storage process. It was thus found that entrapping immobilization pellets have good quality with no impairment caused by the process for storing entrapping immobilization pellets according to the present invention.

4) Wastewater Treatment Test (Operation Conditions for Treatment Tank)

Test wastewater: Ammonium nitrogen-containing inorganic wastewater (containing 40 mg/L of $NH_4$—N)

Packing ratio of entrapping immobilization pellets: 10%

Water temperature: 20° C.

Retention time: Three hours

Figure 6:
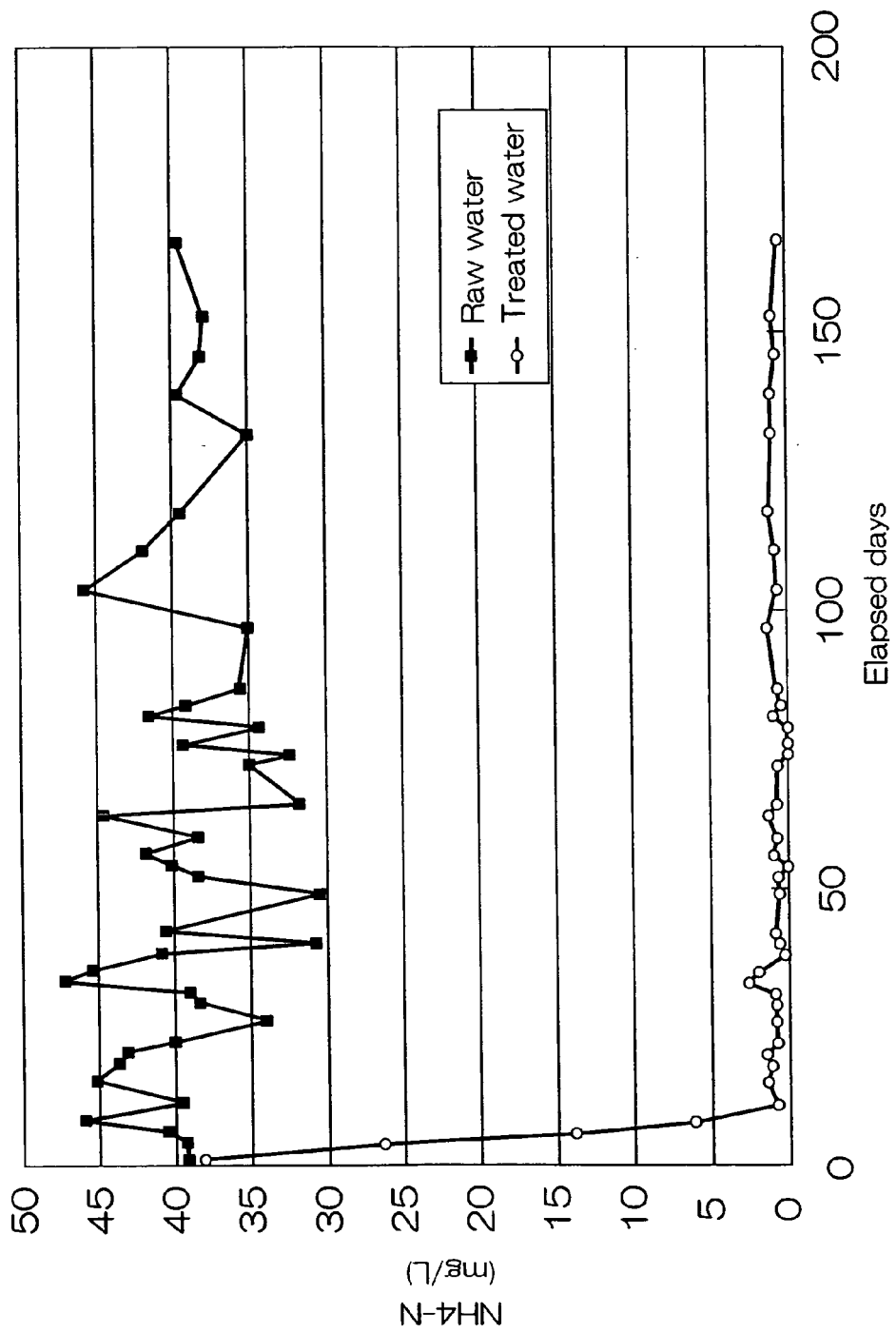
FIG. 6 is a graph for the example.

Ammonium nitrogen was measured by ion chromatography as a sewage testing process. FIG. 6 shows a graph for the wastewater treatment test.

As shown in FIG. 6, the ammonium nitrogen concentration in treated water was reduced after a continuous operation of 150 days or more, and the entrapping immobilization pellets 30 were confirmed to have stable nitrification performance with a nitrification speed of 125 mg/L-pellet/hour or more and a nitrification rate of 95% or more. Thus, the entrapping immobilization pellets 30 had performance comparable or superior to that of entrapping immobilization pellets stored by a conventional storage process.

What is claimed is:

1. A process for producing pellets in which microorganisms are entrapped and immobilized, the process comprising:
    (a) polymerizing a liquid mixture containing the microorganisms and a material capable of polymerizing into a gel to form a block larger than the pellets for use;
    (b) storing the block in water at 15° C. or less or in air at a relative humidity of 90% or more and a temperature of 15° C. or less until the pellets are used; and
    (c) cutting the stored block into the pellets when the pellets are to be used, wherein
    the block has a bottom length:bottom width ratio of 50 mm:50 mm to 150 mm:150 mm, and the block has a volume of 0.12 liters to 22.5 liters.

2. The process according to claim 1, wherein the block is prepared by polymerizing the liquid mixture containing the microorganisms and the material capable of polymerizing into the gel in a rectangular forming frame, and a length:width:depth ratio of the forming frame is 1:1:1 to 1:1:20.

3. The process according to claim 1, wherein step (c) comprises cutting the block into lattices and cutting the lattices into rectangular pellets.

4. The process according to claim 2, wherein step (c) comprises cutting the block into lattices and cutting the lattices into rectangular pellets.

* * * * *